United States Patent [19]

Darfler

[11] Patent Number: 5,045,468

[45] Date of Patent: Sep. 3, 1991

[54] PROTEIN-FREE CULTURE MEDIUM WHICH PROMOTES HYBRIDOMA GROWTH

[75] Inventor: Frederick J. Darfler, Derwood, Md.

[73] Assignee: Cell Enterprises, Inc., Harrisonburg, Va.

[21] Appl. No.: 394,082

[22] Filed: Aug. 15, 1989

Related U.S. Application Data

[63] Continuation-in-part of Ser. No. 940,942, Dec. 12, 1986, abandoned.

[51] Int. Cl.$^5$ .......................... C12N 5/02; C12N 5/12
[52] U.S. Cl. .......................... 435/240.31; 435/240.27; 435/240.3
[58] Field of Search ............ 435/240.3, 240.31, 240.27

[56] References Cited

U.S. PATENT DOCUMENTS

| | | | |
|---|---|---|---|
| 3,929,582 | 12/1975 | Kellner | 435/3 |
| 4,134,793 | 6/1979 | Terada | 435/18 |
| 4,172,572 | 9/1958 | Yoshimoto et al. | 435/68 |
| 4,562,003 | 12/1985 | Lewicki | 435/7 |

OTHER PUBLICATIONS

Jakoby et al., Methods in Enzymology, vol. LVIII, Cell Culture, pp. 56–71, 1979.
Fischer et al., Hormonally Defined Media, pp. 219–221, Springer-Verlag Berlin, Heidelberg, New York, Tokyo, 1983.
Rasmussen and Toftlund, In Vitro Cellular & Development Biology, 22:177 (1986) Phosphate Compounds as Iron Chelators in Animal Cell Cultures.
Rasmusen et al., J. Cell. Sci., 12:275–186 (1973) Cell Multiplication in Tetrahymena Cultures After Addition of Particulate Material.
Suhr-Jessen et al., Ex. Cell. Res.; 139:457 (1982) Wild-Type and Food Vacuole-Less Tetrahymena Thermophila.
Rasmussen et al., J. Cell. Physiol., 122:155–158 (1985) Utilization of Iron Complexes in An Animal Cell.
Yabe, In Vitro Cell. & Dev. Biol., 23:815 (Dec. 1987) Role of Iron Chelators in Growth-Promoting Effect on Mouse Hybridoma Cells.
ABC Technical Bulletin.
Aug., 1986 Letter to Biotechniques.
Cell Enterprises, Inc. Press Release.
Yabe et al., In Vitro Cell. & Dev. Biol., 22:363 (1986) Enhanced Formation of Mouse Hybridomas without Hat Treatment in a Serum-Free Medium.
Kirk-Othmer, Encyclopedia of Chemical Technology, vol. 5, p. 344 (3d ed. 1979) Some Classes of Chelating Agents.
Kovar and Franek, Biotechnology Lett., (:259–264 (1987) Iron Compounds at High Concentrations Enable Hybridoma Growth.
Basset, et al., Fischer and Wieser, hormonally Defined Media: A Tool in Cell Biology, 219–221 (1983).
Perez-Infante et al., Exper. Cell. Res., 142:325–332 (1982).
Taetle et al., J. Clin. Invest., 75:1061–1067 (Mar. 1985).
Titeux et al., J. Cellular Physiol., 121:251–256 (1984).
Phillips et al., Exper. Cell. Res., 134:297–302 (1981).
Amouric et al., In Vitro, 20:543–548 (1985).
Cleveland et al., J. Immunol. Meth., 56:221–234 (1983).
Darfler et al., J. Cell. Physiol., 115:31 (1983).
Jakoby et al., 1979, *Methods in Enzymology* LVIII, Academic Press, NY, NY, pp. 58, 62–71, 361, and 524.
*ATCC Catalogue of Cell Lines & Hybridomas*, 6th Edition 1988, Rockville, MD, pp. 301–303.
*The Merck Index*, The Merck Co., Rahway, NJ, Nos. 4534, 6748, 8487, 9832, 9833.
Freshney, 1983, *Culture of Animal Cells*, Liss Inc., NY, p. 74.

Primary Examiner—Jacqueline Stone
Assistant Examiner—George C. Elliott
Attorney, Agent, or Firm—Iver P. Cooper

[57] ABSTRACT

A chemically-defined, stable, protein-free medium has been devised which is capable of supporting the growth of lymphoid cells, particularly hybridomas, even in anchorage-independent cultures. Doubling rates are close to those obtained with serum-supplemented media. The medium preferably comprises a nonproteinaceous organo-iron compound, especially a nitroprusside salt, an iron chelator such as EDTA, and a selenium compound, such as selenium dioxide or sodium selenite.

15 Claims, 1 Drawing Sheet

THE MURINE HYBRIDOMA 1410 KG7 WAS SEEDED AT 1×10⁴ OR 5×10⁴ CELLS/mL IN STATIONARY CULTURES IN 25cm² T FLASKS IN 8mL OF EITHER 5% FETAL CALF SERUM/95% RPMI 1640 (□) OR C-12 (CONTAINING 3.7 mg/L SNP) + HAM'S F-12 (O). THE CELL NUMBER WAS ASSESSED ON DAYS 4, 7, 11 AND 13. NO GROWTH WAS OBSERVED IN RPMI 1640 + 3.7mg/L SNP (BASSET MEDIUM) (△).

PROTEIN-FREE CULTURE MEDIUM WHICH PROMOTES HYBRIDOMA GROWTH

This application is a continuation-in-part of U.S. Ser. No. 06/940,942, filed Dec. 12, 1986, now abandoned incorporated by reference herein, the benefit of whose filing date is claimed pursuant to 35 U.S.C. Sec. 120.

BACKGROUND OF THE INVENTION

1. Field of Invention

This invention relates to a protein-free medium for the growth of hybridomas in suspension and spinner cultures.

2. Information Disclosure Statement

Hybridoma growth media typically contain serum. See Koprowski, U.S. Pat. No. 4,196,265; Wands, U.S. Pat. No. 4,271,145; Galfre, U.S. Pat. No. 4,350,683. However, Geltosky, U.S. Pat. No. 4,521,510 cultivated newly fused cells in a undisclosed serum-free medium.

Cleveland, et al., J. Immunol. Meth. 56:221 (1983) describes a protein-free medium for hybridoma cultivation. His basal medium was Ham's F12 and IMDM in 1:1 ratio, supplemented with NaHCO$_3$, streptomycin, alphathioglycerol, and progesterone. For cultivation, was supplemented with two trace element mixtures, providing Cu, Mn, Si, Mo, V, Ni, Sn, Zn, Se, Al, Ag, Ba, K, Cd, Co, Cr, Na, Fe, Ge, Rb and Zr. The medium did not contain any organo-iron compound, any selenium salt, or EDTA. The cells were gradually adapted to the protein-free medium. The tolerance of cells for protein-free conditions, and for rapid changes to protein-free conditions, varied from cell line to cell line. Significantly, all of Cleveland's successes were with cells grown as attached monolayers. Even in media supplemented with insulin and transferring, Cleveland was unable to keep hybridomas alive in stationary suspension culture.

Lymphocytes were cultured by Shive, PNAS 83:9 (1986). Shive requires the toxic HEPES buffer and lacks several amino acids (alanine, asparagine, aspartic acid, cystine, glutamic acid and proline), sodium nitroprusside, ions other than Ca, Fe, K, Mg, and Na, the preferred lipophilic components, and other preferred components. Shive, U.S. Pat. No. 4,499,064 emphasizes the inclusion of HEPES buffer and phytohemagglutinin (a glycoprotein). There is some contradiction between the article and the patent as to riboflavin level. While Shive's medium included EDTA, it did not provide SNP or a selenium compound.

Basset, et al. in HORMONALLY DEFINED MEDIA: A TOOL IN CELL BIOLOGY, 219 (1983) grew L1210 leukemic cells at a seed density of $4 \times 10^4$ cells/ml in RPMI 1640 in the presence of either 10% FCS or of the guanylate cyclase activators hemin or sodium nitroprusside. Bassett's medium did not contain EDTA or a selenium salt. L1210 leukemic cells have different growth requirements than hybridoma cells, as is shown by my observation (See Detailed Description) that Bassett's medium did not support the growth of hybridoma cells HB60 or 1410 at any cell density tested.

Basset, et al. Cancer Res., 46:1644–47 (1986) showed that L1210 cells could grow in the absence of serum and transferring when ferrous sulfate or ferric citrate was provided in a concentration of 1–100 $\mu$M. They also studied the effect of desferrioxamine, an iron chelator, on L1210 cells established in transferring-supplemented serum-free medium, finding that prolonged exposure to desferrioxamine had a detrimental effect on cell viability. The addition of ferric citrate or ferrous sulfate to the desferrioxamine-treated cells reinitiated DNA synthesis, but potassium ferricyanide was much less effective. The reinitiation of DNA synthesis and cell growth by ferric citrate was reversed by the antioxidant propyl gallate. Thus, Basset taught against the combination of an iron chelator such as EDTA or an antioxidant known to inhibit lipid peroxidation induced by iron, with an iron transport compound like SNP.

Several references teach use of inorganic iron salts in defined media containing protein. Perez-Infante and Mather, Exper. Cell Res., 142:325–32 (1982) cultivated anchorage-dependent mouse testicular cell lines in a medium consisting of Ham's 1212, insulin, EGF. Hepes, gentamicin and FeSO$_4$. Taetle, et al., J. Clin. Invest., 75:1061–67 (Mar. 1985) describes growth of HL-60 and KG-1 leukemic cells in a medium consistion of RPMI-1640, insulin, ethanolamine, selenium and ferric nitrilacetate. Titeux, et al., J. Cellular Physiol., 121:251–56 (1984) propagated the erythroleukemia K562 and HEL cell lines in a medium made by combining RPMI-1640, albumin, insulin and ferric ammonium citrate. Titeux discouraged use of iron chelators since they completely inhibited cell growth. Phillips and Cristofalo, Exper. Cell Res., 134:297–302 (1981) grew anchorage-dependent WI-38 (normal human diploid fibroblast-like) cells in MCDB-104 supplemented with EGF, insulin, dexamethasone and ferrous sulfate. Amauric, et al., In Vitro, 20:543–548 (1985) cultivated anchorage dependent HT 29 cells in 1:1 Ham's F12:DMEM supplemented with Hepes, selenium, EGF and ferrous sulfate (or ferrous chloride).

Terada U.S. Pat. No. 4,134,793 discloses the use of sodium nitroprusside in the indophenol test for urea. Terada is pertinent only to the extent that he shows that sodium nitroprusside is a known compound. Terada does not, however, use it to support the growth of cells. Terada disrupts bacterial cells before adding SNP to the lysate. It would not be obvious from Terada's work to use SNP in a culture medium.

Kellner U.S. Pat. No. 3,929,582 discloses the use of ferric ammonium citrate in a bacterial cell culture. However, the nutritional requirements of bacterial cells are different from those of hybridoma cells, hence, its use in cultivating hybridomas would not be obvious from Kellner's teaching.

Yoshimoto, U.S. Pat. No. 4,172,572 cultured hybridomas in spinner culture, however, he used an RPMI-1640 medium containing 10% FCS.

Jakoby, et al., Methods in Enzymology 58:62–71 (1979) summarizes the composition of 27 different culture media. Of all of these media, only one, Higuchi's, is said to contain EDTA. However, the same table reveals that it lacks selenium. Only the MCDB family of media (301, 105, 202, 501, 401 and 411) were declared to contain selenium, but, of course, they do not include EDTA. None of Jakoby's 27 media contain sodium nitroprusside.

Torney, U.S. Pat. No. 3,887,430 and US 4,055,466 describe a chemically defined protein-free medium comprising sugar, amino acids, mineral salts; vitamins, a water-soluble lipid source (preferably a polysorbate, but may be sodium oleate or stearate) and a basic anion exchange resin. This medium was used for chick embryo tissue culture and to support the anchorage-dependent MDBK cell line. The resin may hinder subsequent purification steps.

Serum-free media are well known. That of Stemerman, U.S. Pat. No. 4,443,546 contained EGF, Cohn fraction IV, thrombin, insulin, transferring and/or ECGF.

Cartaya, Re 30,985 describes a serum-free medium which contains insulin and therefore is not protein free. It is noteworthy that it presents a riboflavin level of 0.1 mg/L, and that it contains lipophilic components (linoleic, linolenic, or arachidonic acid).

The culture medium of Yamane, U.S. Pat. No. 4,533,637 contains insulin and transferring. Riboflavin is present at 0.4 mg/L. The lipophile provided is linoleic, oleic, linolenic, palmitic or stearic acid. Cyclodextrin is a preferred component.

Baker, U.S. Pat. No. 4,560,655 emphasizes use of a phosphatidylcholine as a lipid source. The other major components of his medium are fetuin and transferrin. Riboflavin is provided at a concentration of 0.4 mg/L.

Fabricius, U.S. Pat. No. 4,406,830's serum-free medium contained only one protein, his novel 90 Kd glycoprotein.

The serum-free medium of Tomei, U.S. Pat. No. 4,049,494 contains 0.1 mg/L of riboflavin. There is no reference to use of proteins.

Yabe, In Vitro Cell. & Dev. Biol., 23:815 (Dec. 1987) favors use of weak iron chelators as transferrin substitutes in serum-free growth of hybridomas. His medium contained selenium but not SNP. Use of EDTA wa reported to have inhibited cell growth, leading to cell death.

No admission is made that any of the foregoing constitute prior art. All references are incorporated by reference to the extent pertinent.

SUMMARY OF THE INVENTION

This invention relates to a novel, protein-free medium which will support the growth of hybridomas and other lymphoid cells. Hybridomas are the products of the fusion of an immortalized cell with an antibody-producing cell. All cells descended from a particular fused cell will secrete the same antibody, which may then be purified from the medium. Since antibodies are proteins, the presence of other proteins in the medium may complicate the purification process. Monoclonal antibodies secreted into my protein-free medium may be purified readily by ultrafiltration or salt fractionation.

This medium is suitable for use in a variety of environments, including hollow fiber ultrafiltration devices, stationary cultures, suspension cultures, spinner cultures, and ceramic-support perfusion systems. However, in view of the limitations of prior protein-free media in supporting unattached (anchorage-independent) cells, it is particularly valuable in suspension and spinner culture.

Like other media, this medium contains amino acids, mineral salts, vitamins and carbohydrates. However, it is noteworthy in several respects.

First, it contains a growth-enhancing amount of a nonproteinaceous organ-iron compound. The preferred compound is sodium nitroprusside, whose presence is believed to have made possible the omission of transferrin.

Second, it contains ethylene diaminetetraacetic acid (EDTA), a chelating agent. It is believed that the ability of EDTA to chelate iron ions helps to protect the cells from their toxic effects. (Iron is implicated in free radical lipid peroxidation). Other iron chelating agents, including other strong chelators of iron (affinity constant log K for ferric ion >14), are expected to have similar utility.

Third, it contains a source of selenium, such as the salts $Na_2SeO_3$ or $SeO_2$.

These three components—SNP, EDTA, and a selenium salt—have a markedly synergistic effect on the growth of hybridoma cells in protein-free medium at low seed densities.

The medium has also been formulated so as to reduce the rate of peroxide generation. Peroxides and their byproducts cause cell damage and death. The conventional HEPES buffer was replaced by MOPS (3-[morpholino]-1-propane sulfonic acid) and riboflavin level was reduced to 0.038 mg/L. Further, two known antioxidants, beta-carotene and alpha-tocopherol acetate, were included.

While the riboflavin level of RPMI 1640 (0.2 mg/L) is known to be undesirable, it is possible that levels of riboflavin as high as 0.1 mg/L would be acceptable, at least for some cell lines, particularly if alpha-tocopherol acetate or beta-carotene are present in the medium. These two substances may exert an antioxidative effect. Alternatively, other antioxidants might be used to shield the cells from peroxide attack. However, a riboflavin level of 0.038 mg/L is preferred. The riboflavin and antioxidant levels would be expected to be more critical for spinner cultures because of the increased exposure to oxygen.

While the value of lipophiles in culture media has been recognized, my medium contains at least one of the following lipophilic compounds: distearoyl phosphatidylcholine, dilinoleoyl phosphatidylcholine, alpha-tocopherol acetate, and beta carotene.

In addition to MOPS, my medium is buffered by 2200 mg/L sodium bicarbonate.

Additionally, my medium contains other components rarely or never found in conventional tissue culture media: progesterone, flavin adenine dinucleotide, L-ornithine, taurine, phosphor (enol) pyruvate.$Na_3.H_2O$, citric acid, spermidine $(PO_4)_3$, L-citrulline and oxaloacetic acid.

Finally, my medium provides various trace elements. As a result of these improvements it was possible to provide a medium in which the doubling time of mouse hybridomas was within 16 hours of that obtained with 10% FCS/90% RPMI 1640 during log phase growth of those cells, even at cell densities of about $1 \times 10^4$.

The deletion of insulin, transferrin and HEPES significantly reduces the costs of the chemical components of the medium. The deletion of transferrin and albumin, both serum-derived proteins, also significantly reduces the chance of carry-over of microbiologic agents into the medium.

DETAILED DESCRIPTION OF THE PREFERRED EMBODIMENTS

Example 1

Media Preparation

Figure 1:
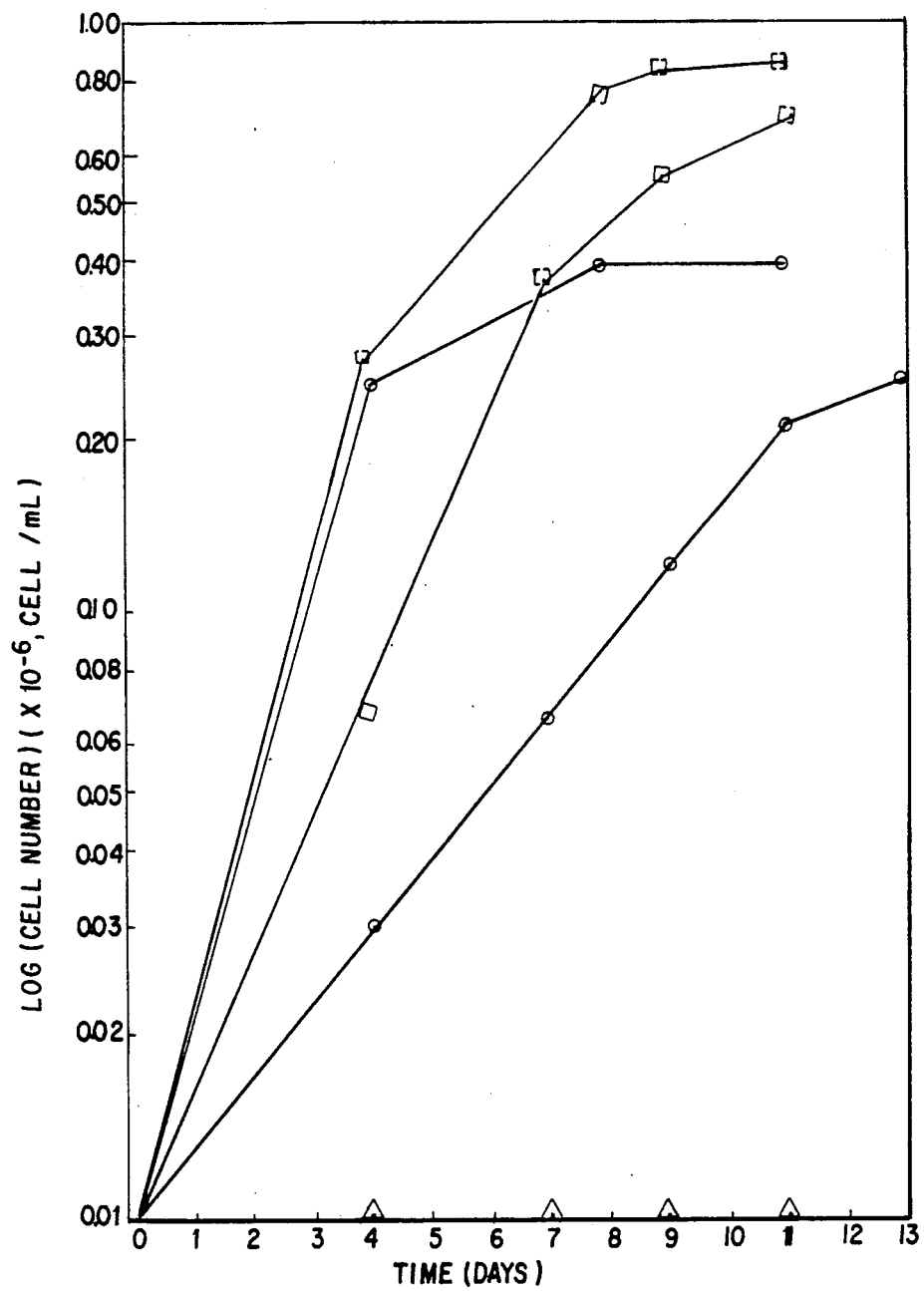
FIG. 1 shows comparative growth of a murine hybridoma (1410 KG7, ATCC HB43) in three different media: (a) 95% RPMI 1640+5% FCS (squares); (b) C-12 containing 3.7 mg/L SNP +Ham's F-12 (circles); and (c) RPMI 1640+3.7 mg/L SNP (Basset medium) (triangles). The hybridoma was seeded at $1 \times 10^4$ or $5 \times 10^4$ cells/ml in 8 ml medium in 25 cm$^2$ T flasks, and cell number was assessed on days 4, 7, 9, 11, and 13.

A noteworthy feature of the present invention is the substitution of sodium nitroprusside for the irontransport protein transferrin. Preferably, SNP is used at a concentration of 2-9 mg/L, the most preferred value being about 5.7 mg/L.

I have found that several other nonproteinaceous organo-iron compounds are suitable as transferrin substitutes (with preferred concentrations stated):
hemin, at 0.3-0.6 mg/L;
ferric nitrilo triacetic acid, at 1.2-6.0 mg/L;

All of these showed some growth-promoting activity. These compounds are structurally dissimilar but have in common an organic moiety capable of tightly binding ("chelating") iron. It is also believed that they have the ability to penetrate the cell membrane. Inorganic iron-containing compounds such as ferrous sulfate are also growth promoters but are rapidly oxidized to the ferric (III) form in ordinary tissue culture medium at neutral pH. The growth enhancement of inorganic iron compounds is only seen when these compounds are added "acutely"; hence the medium in unstable and unsuitable for commercial media which must undergo 2-3 weeks of storage prior to sale according to Good Manufacturing Practices.

The culture medium of the present invention, in its most preferred form (C-12) has the following components:

TABLE I

| Components of C-12 | (mg/L) |
|---|---|
| 1. DL-6,8 Thioctic acid (Sig T5625) | 1.0 |
| 2. Progesterone (Sig P0130) | 0.006 |
| 3. Niacinamide (Sig N3376) | 6.5 |
| 4. Phosphatidylcholine, distearoyl (Av 850365) | 0.5 |
| 5. Phosphatidylchline, dilinoleoyl (Av 850385) | 0.5 |
| 6. Tween 80 (Sig P1754) | 0.2 |
| 7. alpha-Tocopherol acetate (Sig T3001) | 0.15 |
| 8. beta-Carotene (Sig C9750) | 0.05 |
| 9. FAD (Sig F6625) | 0.02 |
| 10. MOPS (USB 19256) (14mM) | 3135 |
| 11. Phenol red (Sig P4633) | 3.0 |
| 12. L-Isoleucine (Sig I2752) | 100 |
| 13. L-TyrosineN$_2$ (USB 22927) | 20 |
| 14. L-Phenylalanine (Sig P2126) | 50 |
| 15. L-Histidine (Sig H8125) | 50 |
| 16. L-Tryptophan (Sig T0254) | 3.0 |
| 17. D-Pantothenic acid, Ca (Sig P2250) | 3.0 |
| 18. Biotin (Sig B4501) | 0.1 |
| 19. L-Valine (Sig V0500) | 79 |
| 20. L-Lysine (Sig L5626) | 72 |
| 21. L-Asparagine.H$_2$O (Sig A8381) | 19 |
| 22. L-Ornithine.HCl (Sig 02375) | 8 |
| 23. L-Leucine (Sig L8000) | 70 |
| 24. NaH$_2$PO$_4$ (Sig S0751) | 250 |
| 25. EDTA (Sig ED4S) | 5.5 |
| 26. Sodium nitroprusside (S S0501) | 5.7 |
| 27. Taurine (Sig T0625) | 30 |
| 28. Phosphor(enol)pyruvate.Na$_3$.H$_2$O (Sig P7002) | 1.0 |
| 29. alpha-Ketoglutarate (Sig K1750) | 25 |
| 30. Citric acid (Sig C0759) | 25 |
| 31. Spermidine (PO$_4$)$_3$ (S0381) | 0.5 |
| 32. Adenine (Sig A8626) | 0.1 |
| 33. alpha-D-Glucose (Sig G5000) | 1600 |
| 34. L-Glutamine (USB 16285) | 250 |
| 35. L-Citrulline (Sig C7629) | 5.0 |
| 36. Pyridoxal.HCl (Sig P-9130) | 0.14 |
| 37. Li$_2$SO$_4$ (Sig L6375) | 10 |
| 38. Ethanolamine.HCl (Sig E6133) | 3.0 |
| 39. Oxaloacetic acid (Sig 04126) | 5 |
| 40. Thymidine (Sig T9250) | 0.07 |
| 41-45. Trace elements I | 5 uL |
| 46-56. Trace elements II | 5 uL |
| 57. Na$_2$SeO$_3$ (Sig S1382) | 0.003 |
| 58. NH$_4$VO$_3$ (Sig A8649) | 0.0006 |

Trace elements I: 2 · 10$^5$ stock to yield (in mg/L final concentration): 0.0002 NiCl$_2$, 0.0001 Na$_2$MoO$_4$, 0.00001 SnCl$_2$, 0.0001 MnCL$_2$ and 0.00013 CuSO$_4$.
Trace elements II: 2 · 10$^5$ stock (mg/L): 0.001 AlCl$_3$.H$_2$O, 0.0002 AgNO$_3$, 0.002 Ba(C$_2$H$_3$O$_2$)$_2$, 0.0001 KBr, 0.002 CoCl$_2$.6H$_2$O, 0.001 Cr(SO$_4$)$_3$.15H$_2$O, 0.004 NaF, 0.0005 GeO$_2$, 0.0001 KI, 0.001 RbCl and 0.001 TiO$_2$.
Sig: Sigma Chemical Corporation, St. Louis, MO.
USB: United States Biochemical Corporation, Cleveland, Ohio.
AV: Avanti Polar Lipids, Inc., Birmingham, AL.

The above-described medium is preferably prepared as described below.

Prepare 14 L of Millipore water of over 7 megohms resistance, collected into HCL/water-washed glass carboys. Prepare Trace Elements for 2000L using 1 ml each Trace Elements stock solutions (2-10$^5$ x) plus 6 mg Na$_2$SeO$_3$, 1.2 mg Nh$_4$VO$_3$ and 100 mg NaH$_2$PO$_4$ (1 g in 1 ml H$_2$O at pH 7.4 with 3 N NaOH; bring vol. to 3 ml and use 0.3 ml). Lyophilize and crush the lyophilized material with 2 g glucose.

Heat sterilize 25×500 ml bottles and autoclave the caps. Weight out the tyrosine (14.4 g), isoleucine (60 g), adenine (60 mg) and biotin (53 mg) [components 13, 12, 32 and 18]and dissolve in 8 L water. Add 0.63g of the trace elements above. Add the rest of a the non-lipid reagents [components 9-11, 14-17, 19-31 and 33-40]. Stir. Periodically add NaOH pellets to yield pH 6.85. Weigh out and pool the lipid components: 0.6 g thioctic, 120 mg Tween 80, 90 mg alpha-tocopherol acetate, 3.6 mg progesterone, 3.9 g niacinamide in 30 ml 99% ethanol. Warm to 40° C. to dissolve. Weigh out and pool: 300 mg DiSPC and 30 mg beta-carotene in 15.0 ml of 20 mg/ml DiLPC in CHCl$_3$. Dry the CHCl$_3$-lipids with N$_2$ to 2.0 ml. Warm both lipid solutions to 40° C. and add the CHCl$_3$ to ethanolic (keeping it warm all the time).

Add water to bring the final volume to 12 L. Readjust the pH to 6.85. With rapid stirring, slowly add the warm lipids. Immediately filter the C-12 through a Gelman 12141 (0.2 um) filter. Collect in 500 ml glass bottles (Wheaton) previously NaOH/HCl/water-washed and heat-treated/sterilized. This method prepares the 50x C12 concentrate, a supplement to Ham's F-12.

The medium can be prepared in powder form (CF-12) although some loss of growth-promoting activity is then experienced. The trace elements are lyophilized with sodium phosphate and crushed with glucose. The lipophilic reagents are dissolved in ethanol with niacinamide. DiSPC, beta-carotene and DiLPC are solubilized in CHCl3 and added. The lipids are dried, lyophilized and crushed with glucose. The rest of the components are added to the trace elements and lipids and milled overnight. To 28.6 g powder, 60.0 g of Media-Tech Ham's F-12 is added and the combined powder milled overnight.

The advantages of the powdered medium are that it can be prepared in large quantities inexpensively, shipped easily and inexpensively, and sold without filtration.

The CF-12 protein-free powdered medium is readily reconstituted.

Measure out 90% of the water (highest quality, tissue culture grade) necessary for the desired volume. All containers should be of high quality glass that is first rinsed with 0.1 N NaOH, 1 N HCl and water.

Add the appropriate amount of CF-12 (14.8 g/L) to the water. Add 2.2 g/L sodium bicarbonate. Stir until dissolved and adjust pH to 6.85. Add additional water to reach final volume. Sterile filter using positive filtration (0.2 um) with detergent-free filters. Aseptically dispense into sterile glass containers. Store tightly capped in the dark at 2–8° C. Use within 2 weeks. If exposure of the powder to air results in crusting and/or color change further use of the product is not recommended.

When reconstituted, CF-12 contains L-glutamine which has a half-life of 3 weeks at 4° C. Extended shelf-life can be obtained by over-laying the medium with $CO_2$ before storage.

The full activity of CF-12 may be restored by the addition of 1 ug/ml human transferrin plus 2 ug/ml bovine insulin, however, the medium then is not protein-free.

It will be recognized that certain components may be deleted, though possibly with some loss of growth-supporting activity, without rendering the medium useless for its intended purpose. The removal of a single component may merely force the cells to produce a necessary substance by an alternate metabolic pathway.

C-12, when added to Ham's F-12, is able to support the growth of hybridomas and other lymphoid cell lines even at low and clonal cell densities. No adaptation is necessary. The supplement in Ham's F-12 can also be used for in vitro immunization of murine splenocytes. The lack of protein in the medium allow the use of antigen in the ng/ml range. The medium is particularly suited for the production of monoclonal antibodies from hybridomas. A simple salt fractionation or concentration by ultrafiltration results in over 90% pure antibody.

Mouse x mouse, rat x mouse and human x mouse hybridomas, human HL-60, WIL2-derived lines, IM-9, Daudi L1210 and MOLT-4 cells all grow well in C-12 plus Ham's F-12. In addition, other "monolayer" cultures may grow in an anchorage-independent mode. Certain cell lines such as P3-N21-Ag-4 (NS1) may require low density lipoproteins for growth.

To use C-12:

1. Warm 500 mL Gibco liquid Ham's F-12 basal medium (cat. No. 320-1765) to 37° C. Add 1.0 g/L sodium bicarbonate from a sterile-filtered 7.5% stock solution. Add 10 mL C-12.

2. Pre-equilibrate culture vessel (T flask or spinner flask) with 5% $CO_2/95\%$ air. Dilute hybridomas or lymphoid cells with protein-free medium and incubate at 37° C. in 5% $CO_2/95\%$ air 100% humidified incubator.

3. Alternatively, autoclave 450 ml tissue-culture grade water at 250° F., 15 PSI, 1 hr. Cool to 37° C. and add 20 ml of 25x Ham's F-12 medium, 10 ml C-12 and 15 ml sterile 7.5% sodium bicarbonate. Culture cells as above. Preparation of 25× Ham's F-12 ("A-12") Dissolve 319.4 gm Mediatech Ham's F-12 medium, cat. No 50-040-PB in 12L high quality water. Let stand 1 hr. Without disturbing sediment, sterile filter through 0.2 um Gelman 12141 filters and bottle in 100 and 500 mL volumes. To use C-12 for Spinner culture growth in the most preferred embodiment of use:

1. Use Bellco spinner flasks, series 1965 (microcarrier blades). For 15–30 L volumes, trim blades to 5 approximately 9 in 2.

2. Use Bellco stirrers (micro-carrier) at 16 RPM (15 30L) or 20 RPM (smaller sizes). Culture cells at $0.1-0.4 \times 10^6$ cells/ml, feeding with fresh medium as needed daily. At required volume, stop feeding and harvest conditioned medium when cell growth ceases.

3. For over 6L cultures, headspace must be continually flushed with 5% $CO_2/95\%$ air to keep oxygen supply high. Increase oxygen content of gas mixture for cultures over 15L.

In modifying the preferred medium, persons skilled in the art may find it helpful to keep in mind the following comments regarding the components. However, this invention is not dependent on any particular theory concerning the function of these substances:

1. L-Ornithine is a precursor of putrescine, L-arginine, L-citrulline and L-glutamic acid. It is a "nonprotein" amino acid. It's found in the blood at 5 mg/L and was tested for that reason.

2. Lithium (sulfate or chloride) has been shown to enhance the growth of human leukemia cells (L.E. Gauwerkry and D.W. Golde, *Brit. J. Haematol.*, 51:431 (1982)). The action of lithium in this regard is unclear.

3. Taurine (ethanolamine sulfonic acid) probably serves as a precursor for ethanolamine for the synthesis of phosphatidyl ethanolamine. Taurine has been used in other serum-free media, e.g. M. Koga, *Fed. Proc.*, 45: 853 (86).

4. L-Citrulline is present in the blood at 9 mg/L and was tested as a result. It is a precursor to L-arginine.

5. Tween 80 is an oleic acid-containing detergent that historically has been used to aid in the solubilization of hydrophobic (especially lipid) compounds, e.g. V.J. Evans et al., *Cancer Res.*, 16:77–94 (1956) for NCTC 135 medium. The oleate may also provide essential unsaturated fatty acids. Other detergents such as Pluronic F-68 (nonionic surfactants) may also substitute for Tween 80.

6. Flavin adenine dinucleotide is a riboflavin-containing compound which functions as a prosthetic group for oxidation/reduction enzymes (flavoproteins). Flavoproteins function in the degradation of pyruvate, fatty acids and amino acids. That FAD has less peroxideforming capabilities than does riboflavin remains a possibility. FAD has been used in tissue culture media for many years, e.g. R.C. Parker et al., Special Publications, N.Y. Academy of Science, 5:503 (1957).

7. Oxaloacetate (see 9 below).

8. Citrate (see 9 below).

9. Alpha-Ketoglutarate (and oxaloacetate and citrate) are all members of the tricarboxylic acid (TCA) or Kreb's cycle. Each can serve as precursors to various amino acids. In addition, they can serve as carbon skeletons onto which ammonia may be fixed (forming amino acids) thereby removing toxic ammonia from the culture medium. The level of ammonia can limit the "saturation" density of suspension cell cultures. Succinate, malate and isocitrate may also substitute for the above. Holmes medium (R. Holmes, *Biophys. Biochem. Cytol.*, 6:535 (1959)) contains citrate; Schneider's medium (J. Exp. Zool., 156, 91–104 (1964)) contains alpha-ketoglutarate.

10. PEP can form pyruvate and ATP, catalyzed by pyruvate kinase. The growth-enhancing effect of PEP was demonstrated by Bettger, et al., *Proc. Natl. Acad. Sci. USA*, 78, 5588–5592 (1981).

11. MOPS is a buffer similar to the more commonly used HEPES buffer. MOPS does not have a piperazine ring moiety, however, and does not augment riboflavin/tryptophan-induced peroxide formation. BisTris and other buffers can also replace HEPES.

12. Beta-Carotene absorbs ultraviolet and visible radiation and may prevent light from reaching riboflavin, hence preventing peroxide formation. Alpha- and gamma-carotene may also be effective. Beta-Carotene is the precursor to vitamin A.

13 Alpha-tocopherol acetate was used by Bettger in the preparation of an additive to a defined medium for the growth of human diploid fibroblasts (W.J. Bettger et al., see above). Alpha-tocopherol acetate is a stable form of alpha-tocopherol and is inert until it is hydrolyzed after entering the cell, whereupon it may have antioxidative effects.

14. Spermidine may serve to stabilize ribosomes and DNA. The level of spermidine in the blood is 1 mg/L and it was tried for this reason.

15. SNP is an organo-iron compound bearing iron in the ferric state. All cells in serum-free medium have an absolute requirement for iron. Iron can be delivered in one of three forms: (1) bound to transferrin, (2) as the ferrous form (organic or inorganic) or (3) as a nonproteinaceous, organo-iron compound (usually in the ferric form). Ferrous forms are readily oxidized at neutral pH to the ferric form. Hemin, ferrocene, ferric ammonium citrate, ferric nitrilo triacetate may be substituted for SNP but are not preferred.

16. Distearoyl phosphatidyl choline: Hybridomas and other lymphoid cells grow faster in the presence of a certain amount of saturated fatty acids. Often palmitic acid complexed to albumin is used for this purpose. Solubility problems of the fatty acids are partially overcome by the use of phosphatidates containing palmitic, stearic, lauric, or myristic acids. Besides PC, phosphatidyl ethanolamine and phosphatidyl serine and others may be effective substitutes. Murakami et al., in *Growth of Cells in Hormonally Defined Media*, 9:711-715 (G.H. Sato et al., eds., Cold Spring Harbor Laboratory (1982)) showed that impure phosphatidates promoted the growth of hybridomas in serum-free medium.

17. Dilinoleoyl phosphatidyl choline: Many lymphoid cells, including most hybridomas, require the presence of unsaturated fatty acids for growth. Linoleic or oleic acid in some form must be supplied; as free fatty acids these are toxic to cells in albumin-free medium. Phosphatidyl choline with one or more of its fatty acids being unsaturated allows higher levels of these fatty acids to remain in solution in nontoxic amounts. Phosphatidyl ethanolamine, phosphatidyl serine, etc. may substitute for PC. The use of DiLPC for serum-free medium was shown by F.J. Darfler and P.A. Insel, *J. Cell. Physiol.*, 115, 31-36 (83).

Example 2
Support of Hybridomas by Preferred Medium

A medium according to the invention (which differed from the preferred medium only in that it used 3.7 mg/L SNP) supported the growth of the murine hybridoma, 1410 KG7, in stationary (T flask) cultures. Cells seeded at $1 \times 10^4$ and $5 \times 10^4$ cells/mL grew with doubling times of 60.6 hrs and 42.4 hrs respectively. Growth in serum was 37.7 hrs and 38.6 hrs, respectively. The 1410 KG7 cells failed to grow in Basset's medium at $1 \times 10^4$ cells/mL. More rapid growth was obtained using C-12 plus Ham's F-12 using 5.7 mg/L SNP (shown below).

The preferred medium also supported the growth of the murine hybridoma L243 (ATCC HB55) in spinner culture. The murine hybridoma, L243, was grown in T flasks in proteinfree medium (C-12 plus Ham's F-12) to 400 ml. The culture was transferred to a 1 L spinner flask (Bellco) equipped with a micro-carrier spinner assembly. The stir rate was 20 rpm in a 5% $CO_2$/95% air, 37° C. environment.

TABLE II
Growth of L243 in Preferred Medium

| Day | Cell No (cells/ml) | Culture vol. | Total Cell No. |
|---|---|---|---|
| 1 | $0.072 \times 10^6$ | 400 mL | $28.8 \times 10^6$ |
| 2 | $0.141 \times 10^6$ | 400 mL | $56.4 \times 10^6$ |
| 3 | $0.131 \times 10^6$ | 550 mL | $71.9 \times 10^6$ |
| 4 | $0.202 \times 10^6$ | 550 mL | $111.1 \times 10^6$ |
| 5 | $0.246 \times 10^6$ | 790 mL | $194.6 \times 10^6$ |
| 6 | $0.380 \times 10^6$ | 1080 mL | $410.4 \times 10^6$ |

The murine hybridoma, L243, was grown in T flasks followed by spinner culture as described above to 3.4 L at $0.443 \times 10^6$ cells/ml. 1 L of the culture was centrifuged at 1000 RPM for 30 min to remove cells and the conditioned medium was concentrated to 22 ml by tangential flow ultrafiltration (30,000 Dalton cut-off). Twenty-five mg of protein was collected. Note that the doubling time averaged 37.6 hrs over the 6 days' growth and was 25.5 hrs from day 4 to day 6.

Example 3
Comparison of Responsiveness of L1210 Lymphoid Cells and HB60 Hybridoma Cells L1210 Lymphoid cells and HB60 hybridoma cells markedly differ in their responsiveness to SNP, as is evident from Table III below.

C-12 is beneficial for the growth of L1210 cells at low seed density, however this growth enhancement comes primarily from the inclusion of SNP in C-12; otherwise C-12 appears to be inhibitory to L1210 cell growth (high density F-12 vs F12+SNP). In contrast, for HB60 hybridomas, the marked beneficial effect of C-12 comes not from the inclusion of SNP in C-12, but for other reasons.

TABLE III
EFFECT OF SNP AND C-12 ON THE GROWTH OF L1210 vs HB60 CELLS IN RPMI-1640 vs HAM'S F-12 MEDIA

| Cell Line | Medium | Cell Number ($\times 10^{-3}$, cells/ml) | |
|---|---|---|---|
| | | Low Density | High Density |
| L1210 | RPMI | 16 (15%) | 1830 (80%) |
| (mouse | RPMI + SNP | 58 (60%) | 1450 (70%) |
| lymphocytic | Ham's F-12 | 21 (10%) | 1110 (40%) |
| leukemia) | Ham's F-12 + SNP | 139 (70%) | 1130 (25%) |
| | Ham's F-12 + C-12 | 229 (70%) | 1020 (20%) |
| HB60 | RPMI | 1.6 (0%) | 16 (0%) |
| (mouse | RPMI + SNP | 1.7 (0%) | 22 (25%) |
| B × B cell | Ham's F-12 | 3.2 (0%) | 42 (45%) |
| hybridoma) | Ham's F-12 + SNP | 3.0 (0%) | 44 (50%) |
| | Ham's F-12 + C-12 | 70.0 (90%) | 586 (95%) |

The numbers in parentheses indicate cell viabilities.
SNP: $Na_2Fe(CN)_5NO$ at 2.7 mg/L
RPMI - SNP is Basset's medium.
C-12 contained 5.7 mg/L SNP.
The seed densities were $1 \times 10^4$ and $8 \times 10^4$ cells/mL for L1210 cells and $5 \times 10^3$ and $4 \times 10^4$ cells/mL for HB60 cells.
Cells were grown in T flasks in 8 mL volumes and cell number assessed after 5 days' growth.
The doubling time of HB60 in Ham's F-12 + C-12 was 31.5 hr at low density and 31.0 hr at high density.

Because there are marked differences between L1210 cells and HB60 hybridomas, even though both cell lines are of murine lymphocytic origin, one has to conclude that the requirements for amino acid, vitamins, lipids, mineral salts and other components must vary from cell line to cell line depending on the lineage of thsoe lines eevn within a general tissue lineage such as "lymphocytic". This is in accordance with the views of Ham (R.G. Ham, in *Hormonally Defined Media*, G. Fischer and R.J. Weiser, eds., 1983, Springer-Verlag, Berlin, pp. 16-30).

Example 4

Relative Contributions of Media Components to Hybridoma Growth

The hybridoma OKT3 was seeded at $5 \times 10^3$ cells/ml in 2 ml in 24 well plates (in triplicate wells) in the presence or absence of the reagents indicated below. Cell number was assessed six days after seeding. The cell viability on day 6 in wells containing Ham's F12 alone was under 1%. The abbreviation "TESE" refers to "trace elements plus selenium dioxide", the "trace elements" being a combination of "trace elements I" and "trace elements II" of C-12.

TABLE IV

| Medium | ($10^3$ cells/ml) Cell No + SEM | Relative Cell Growth |
|---|---|---|
| Ham's F12 | 6.08 ± 0.23 | 100 |
| F-12 + SNP | 6.83 ± 0.37 | 112 |
| F-12 + EDTA | 7.52 ± 0.74 | 124 |
| F-12 + TESE | 6.51 ± 0.46 | 107 |
| F-12 + SNP + EDTA | 8.32 ± 1.02 | 137 |
| F-12 + EDTA + TESE | 8.11 ± 0.78 | 133 |
| F-12 + SNP + TESE | 13.07 ± 1.16 | 225 |
| F-12 + SNP + TESE + EDTA | 22.40 ± 4.62 | 369 |

It will be seen from the above experiment that the individual effect of SNP, TESE and EDTA on OKT3 growth was modest. However, SNP plus TESE had a synergistic effect, and the use of all three had a further synergistic effect.

Another experiment made it apparent that the most significant TESE component was the selenium compound, and that SNP is superior to both FAC and hemin when these organo-iron compounds are combined with the selenium compound and with EDTA.

TABLE V

| Medium | ($10^3$ cells/ml) Cell No + SEM |
|---|---|
| F12 | 47 ± 15 |
| F12 + SNP | 61 |
| F12 + SNP + EDTA + Se | 175.8 ± 7.2 |
| F12 + SNP + EDTA + Se + Va | 176.3 ± 10.3 |
| F12 + SNP + EDTA + Se + Cu/Cr/Rb | 76.4 ± 2.4 |
| F12 + SNP + EDTA + Se + TE | 172 ± 3.7 |
| F12 + SNP + TE + Se | 135.6 ± 14.4 |
| F12 + EDTA + Se | 39.4 ± 1.3 |
| F12 + Hemin + EDTA + Se + TE | 139.3 ± 16.8 |
| F12 + Transferrin + Se + TE | 79.5 ± 21.3 |
| F12 + FAC + EDTA + Se | 45.3 |

(7 day assay in 24-well plates at 2 ml/well; OKT3 hybridoma)

Example 5

Comparison of Growth of Hybridomas in F12/C12 Medium with Growth in Serum-Supplemented Medium In Table VI below, we see a comparison of the doubling times achieved with hybridomas 1410 and L243 grown in my medium and in a conventional serum-supplemented medium at two different seed densities.

TABLE VI
COMPARISON OF GROWTH OF TWO HYBRIDOMAS IN C-12 PLUS F-12 vs 5% FETAL CALF SERUM/RPMI 1640

| Cell Line | Medium | Culture Conditions | SNP Conc. (mg/L) | Cell Density (cells/ml) | Doubling Time |
|---|---|---|---|---|---|
| 1410 | 5% FCS/RPMI | Stationary | 0 | 1–5 × $10^4$ | 34.7 hrs |
| 1410 | 5% FCS/RPMI | Stationary | 0 | 5–30 × $10^4$ | 38.6 |
| 1410 | C-12 + F-12 | Stationary | 3.7 | 1–5 × $10^4$ | 60.6 |
| 1410 | C-12 + F-12 | Stationary | 3.7 | 5–30 × $10^4$ | 42.4 |
| L243 | 5% FCS/RPMI | Stationary | 0 | 2–20 × $10^4$ | 27.5 hrs |
| L243 | C-12 + F-12 | Stationary | 3.7 | 3–6 × $10^4$ | 42.6 |
| L243 | C-12 + F-12 | Stationary | 5.7 | 1–7 × $10^4$ | 31.5/38.3 |
| L243 | C-12 + F-12 | Stationary | 5.7 | 8–50 × $10^4$ | 31.0 |
| L243 | C-12 + F-12 | Stirred | 5.7 | 7–30 × $10^4$ | 37.6 hrs |

The hybridoma 1410 KG7 is derived from the myeloma Sp2/0-Ag14.
The hybridoma L243 is derived from the myeloma P3/NS1/11-Ag-1.
These two myelomas are used most frequently for the formation of mouse x mouse hybridomas.

I claim:

1. A protein-free culture medium comprising (a) a nonproteinaceous organo-iron compound selected free from the group consisting of a nitroprusside salt and hemin, and (b) a selenium compound, in amounts which, in combination, synergistically promote the growth of hybridomas.

2. The culture medium of claim 1, further comprising EDTA.

3. The culture medium of claim 1, further comprising trace elements.

4. The medium of claim 1 wherein the selenium compound is selenium dioxide.

5. The medium of claim 1 wherein the selenium compound is a selenite salt.

6. The medium of claim 1 wherein the organo-iron compound is a nitroprusside salt.

7. The medium of claim 1 wherein the organo-iron compound is hemin.

8. A method of cultivating hybridoma cells in a protein-free, anchorage independent manner which comprises introducing anchorage-independent hybridoma cells into a protein-free culture medium according to claim 1, and cultivating the cells in the medium in an anchorage-independent manner.

9. The method of claim 8 wherein the cells are cultivated in a spinner culture.

10. The method of claim 8 wherein the cells are introduced into the culture at a seed density of no more than about $10^4$ cells/ml.

11. The method of claim 8 wherein the organo-iron compound is a nitroprusside salt.

12. The method of claim 8 wherein the organo-iron compound is hemin.

13. The method of claim 8 where the culture medium further comprises EDTA.

14. The method of claim 11 where the culture medium further comprises EDTA.

15. The method of claim 12 where the culture medium further comprises EDTA.

* * * * *